Figure 1:
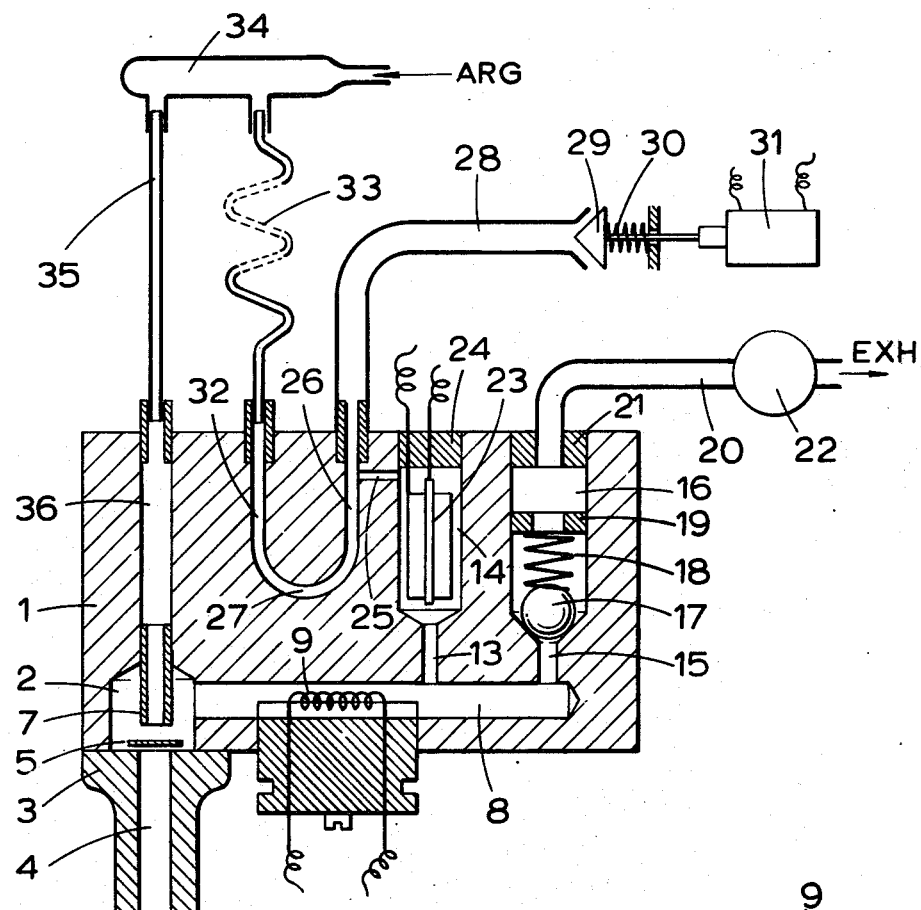

United States Patent [19]

Bradshaw

[11] 4,166,379

[45] Sep. 4, 1979

[54] APPARATUS FOR THE DETECTION OF VOLATILE ORGANIC SUBSTANCES

[75] Inventor: Robert F. D. Bradshaw, Cambridge, England

[73] Assignee: Pye Limited, Cambridge, England

[21] Appl. No.: 868,064

[22] Filed: Jan. 9, 1978

Related U.S. Application Data

[63] Continuation of Ser. No. 781,933, Mar. 28, 1977, abandoned, which is a continuation of Ser. No. 664,531, Mar. 8, 1976, abandoned.

[30] Foreign Application Priority Data

Mar. 11, 1975 [GB] United Kingdom ............... 10054/75

[51] Int. Cl.² .................... G01N 27/62; G01N 31/06
[52] U.S. Cl. ......................................... 73/23; 422/88;
422/90; 422/98; 250/383
[58] Field of Search ............ 23/232 R, 232 E, 232 C;
73/23, 25, 26, 27 R; 422/83, 88, 90, 94, 98;
250/383

[56] References Cited

U.S. PATENT DOCUMENTS

| | | | |
|---|---|---|---|
| 1,467,084 | 9/1923 | Bassett | 73/27 R |
| 2,904,406 | 9/1959 | Moore | 23/232 E |
| 3,068,402 | 12/1962 | Redhead | 73/23 X |
| 3,883,739 | 5/1975 | Jenkins | 422/90 X |

Primary Examiner—Joseph Scovronek
Attorney, Agent, or Firm—Thomas A. Briody; Edward J. Connors, Jr.

[57] ABSTRACT

An apparatus for detecting the presence of volatile, organic substances in gaseous mixtures comprises a filament on which the substances are absorbed when the filament is cold and released when hot, an electron capture device to detect the emitted substances, a primary and a secondary flow of inert gas, and a valve system in which system an inlet valve which admits the gaseous mixture automatically closes when the gas pressure of the gases within the apparatus exceeds the ambient pressure, the presence of the volatile organic substances being indicated by an output signal from the electron capture device. The apparatus alternatively may be used for controlling the flow of gases containing organic volatile substances.

The filament may be sensitive to specific vapors.

10 Claims, 3 Drawing Figures

U.S. Patent     Sep. 4, 1979     4,166,379

APPARATUS FOR THE DETECTION OF VOLATILE ORGANIC SUBSTANCES

This is a continuation application of Ser. No. 781,933, filed Mar. 28, 1977, now abandoned; which in turn was a continuation application of Ser. No. 664,531, filed Mar. 8, 1976, now abandoned.

The present invention relates to an apparatus and to a method for controlling the flow of gaseous mixtures which contain volatile organic substances and to the detection of volatile organic substances contained in the gaseous mixtures.

The detection of volatile organic substances in an atmospheric sample is known in apparatus wherein a sample is drawn through a chamber in which is mounted a filament on which volatile organic substances present in the sample are adsorbed. The sample flow is then cut off and is replaced by a flow of an inert gas such as argon. After any residual sample has been purged from the apparatus by the argon flow, an electric current is passed through the filament to raise its temperature and thereby drive off any adsorbed volatile organic substance, which is carried by the argon flow to an electron capture detector located on the downstream side of the filament. The presence of the volatile organic substances is revealed by a change in an output signal of the electron capture detector.

Prior to the present invention known detectors incorporate a motor-driven switch to control the sample and gas flows, the control being achieved by physically altering the configuration of the gas flow passages and, as this involved the use of sliding parts, leakages of the gases constantly presented problems. The known apparatus also required the provision of a driving motor and a servo system for monitoring the control switch.

One object of the present invention is to provide an apparatus for the detection of volatile organic substances contained in gaseous mixtures which automatically draws into the apparatus sample quantities and passes each sample quantity over a filament by pumping means located at the downstream end of the apparatus, there being provided in the apparatus an inlet valve which automatically closes an inlet passage for the gaseous mixture when gas pressure within the apparatus exceeds the ambient pressure, an outlet valve which opens an exhaust passage via an electron capture device to atmosphere and a non-return third valve located in a gas flow path between the filament and a pumping means. Suitable filaments for carrying out the method according to the invention are electrically conductive wires with a high surface reactivity such as platinum, palladium, chromium and nickel and alloys thereof. The surface of the filaments may be treated so as to increase their reactivity to adsorb the volatile organic substances and to release the substances when an electric current is passed through to heat the filament.

According to the present invention there is provided an apparatus for detecting volatile organic substances contained in a gaseous mixture comprising a filament, which absorbs, when cold, the volatile organic substances and releases the substances, when heated, to an electron capture device, a first inlet passage with an inlet valve to admit a quantity of the mixture into the apparatus, a second inlet passage to admit a primary flow of an inert gas for example, argon over the filament, a third inlet passage to admit a secondary flow of the inert gas which passes over the electron capture device when the filament is cold, a first outlet passage with an outlet valve to exhaust the gas under analysis and the inert gas to the atmosphere, a second outlet passage with outlet valve to permit the primary flow of inert gas to take the volatile component released from the filament when heated to the electron capture device, the inlet valve of said first inlet passage being adapted to open when the pressure in the apparatus is less than the ambient pressure and to close when the pressure in the apparatus exceeds the ambient pressure, means to open the outlet valve of said first outlet passage when the pressure in the apparatus exceeds the ambient pressure and means to open the outlet valve of said second outlet passage, the presence of one or more of the volatile organic substances being detected by a change in an output signal from the electron capture device.

Preferably, the inlet valve of the first inlet passage is opened by lowering the pressure in the apparatus below the ambient pressure by a pump situated in the first outlet passage. This valve conveniently is a flap valve. The outlet valve of the second outlet passage is normally closed and the means to open the outlet valve, preferably, is an electrically operated solenoid-valve which is energised when the filament is heated and the valves of the first inlet and the first outlet passages are closed. In particularly preferred embodiment the outlet valve of the first inlet passage is a spring loaded ball valve. The filament as an electrically conductive wire of the aforementioned type may be removably mounted in a duct in the apparatus between the first and second inlet passages and the electron capture device. When the apparatus is used for controlling the flow of a gas mixture, the gas contains one or more volatile organic substances which are capable of being adsorbed on the filament when cold and released when selected for best adsorption and released in accordance with the material used for the filament and the sensitivity of the electron capture device. Control of the flow of the gas is then achieved by a quantity of the gas being drawn into the apparatus and released from the apparatus with the inert gas as hereinbefore described.

The expression "volatile organic substances" for the purpose of the present invention is understood to mean any organic substance which is normally volatile at room temperatures and pressures and which can be adsorbed onto the filament when cold and released into an inert atmosphere such as helium, neon, argon, krypton or xenon and other inert gases such as nitrogen when the filament is heated. The volatile organic substances may be gases in the gaseous sample under analysis which can condense on the filament at room temperatures or they may be vaporized or non vaporized organic solids or liquids emitted, for example, as particles from a quantity of organic substance either alone or with solvents for the substance.

Figure 3:
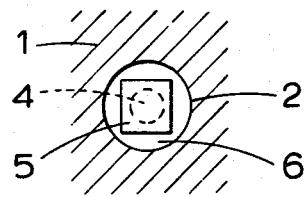
Figure 2:
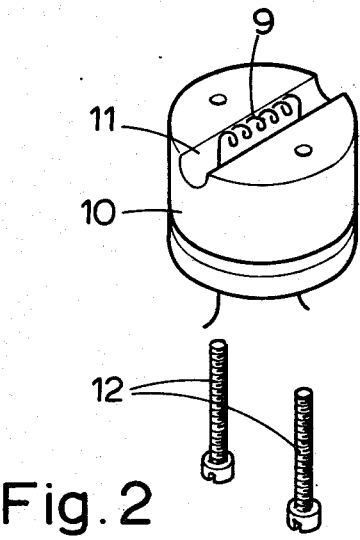

In order that the invention and the manner in which it is to be performed may be more clearly understood, an embodiment thereof will be described by way of example with reference to the attached drawings, of which:

FIG. 1 is a sectional view of vapor detection apparatus according to the invention, FIG. 2 is a perspective view of a filament assembly for use with the apparatus of FIG. 1, FIG. 3 is a plan view of the inlet valve of the apparatus of FIG. 1.

Referring first to FIG. 1, the apparatus comprises a block 1 of inert material, typically polytetrafluoroethylene or P.T.F.E. of generally rectangular shape. Adjacent one end of the block 1 is an inlet valve cavity 2 of circular section and open on one face of the block. A probe 3 which may be a flexible tubular plastic moulding and comprises what is sometimes referred to herein as the "first inlet passage", is secured to the said face of the block so that its bore 4, which is of lesser diameter than the cavity 2 is coaxial with the latter. A valve 5 comprising a thin plate of e.g. MELINEX (a registered Trade Mark) is located within the cavity 2. Preferably the valve 5 (which is sometimes referred to herein as the "first inlet valve") is square in plan as shown in FIG. 3, with sides of a length greater than the diameter of the bore 4 but with a diagonal length slightly less than the diameter of the cavity 2. When pressure in the cavity exceeds ambient pressure the first inlet valve 5 rests on the end of the probe 3 and seals the bore 4. When the pressure in the cavity is below ambient, the first inlet valve 5 rises, permitting gas entering through the bore 4 to pass through the spaces 6 (FIG. 3) between the edges of the valve 5 and the wall of the cavity 2. The lift of the valve 5 may be limited by a tube 7 extending from the top of the cavity 2.

A duct 8 extends from the cavity 2 towards the opposite end of the block 1. A filament 9 is mounted within the duct. Preferably a filament assembly is employed comprising a cylindrical P.T.F.E. plug 10 (FIG. 2) with a recess 11 of semi-circular cross section extending diametrically across one flat face, the filament 9 being supported in the recess by its lead-out wires which pass through the plug 10. The plug 10 fits into a corresponding cavity formed in the lower face of the block 1 and intersecting the duct 8, the arrangement being such that when the plug 10 is in place the surface of the recess 11 (FIG. 2) completes the wall of the duct. The plug is secured by screws 12 entered into holes tapped in the block. This arrangement permits easy changing of the filament 9.

At a point beyond the filament 9 a passageway 13 leads from the duct 8 to the base of a chamber 14 which extends to the upper surface of the block 1, and at a point adjacent the closed end of duct 8 a further passageway 15 leads to the base of a further chamber 16. The base of the chamber 16 is shaped to serve as a seat for a ball 17 of nylon or P.T.F.E. which is urged towards the seat by a spring 18, in turn retained by a collar 19 secured to the wall of the chamber 16. A tube 20 passes through a seal 21 at the upper end of the chamber 16 and extends to a suction pump shown schematically at 22 and thence to exhaust.

It will be seen that when the pressure in the duct 8 sufficiently exceeds that in the chamber 16 the ball 17 will be forced off its seat, but when the pressure difference is small the ball will be held on its seat by the action of the spring 18, so closing the end of the passageway 15. The ball 17 and its associated spring 18 thus serve as a non-return valve (such being sometimes referred to as the "first outlet valve") permitting gas to flow from the duct to the chamber 16 and thence to exhaust via the first outlet passage 20, but preventing any flow in the reverse direction.

The chamber 14 houses an electron capture detector 23 which is carried by a seal 24 closing the chamber at its upper end. A passageway 25, immediately below the level of the seal 24 connects the chamber 14 to an arm 26 of a generally U-shaped passageway 27 formed within the block 1. The upper end of the arm 26 is connected via a tube 28 and valve 29 to atmosphere passageway 25, arm 26, and tube 28 hereinafter sometimes being referred to as the "second outlet passage". The valve 29 (which is sometimes referred to as the "second outlet valve") maybe a plug valve normally held closed by a spring 30 but openable by the energisation of a solenoid 31 whose armature is connected to the valve.

The arm 32 of the U-shaped passageway 27 is connected via a gas flow restrictor 33 to a vessel 34 supplied with argon at a pressure typically of 15 p.s.i. above atmospheric. The restrictor 33, which may comprise a capillary tube of suitable bore and length is adapted to provide a flow of argon (known as the secondary flow) to the passageway 27 at a rate of typically 0.5cc/second.

A primary flow of argon is delivered from the vessel 34 via a second inlet passage comprising a second restrictor 35, a passageway 36 and the tube 7 to the inlet valve chamber 2. The restrictor 35 is adapted to provide a primary argon flow rate of, typically 4.0/second.

Suitable means, not shown in the drawings, are provided for energising at will the solenoid 31 and the pump 22 and for heating the filament 9.

The mode of operation is as follows: Initially the filament 9 is cold, and the pump 22 and solenoid 31 are de-energised so that the second outlet valve 29 is closed. The pressure in the valve cavity 2 is above atmospheric in consequence of the primary argon flow and hence the first inlet valve 5 is closed, sealing the first inlet passageway 4. The pressure in the duct 8 is also above atmospheric so the ball 17 is lifted off its seat and the argon escapes to atmosphere via the tube 20 and leakage paths through the stationary pump 22. It may be noted that under these conditions the secondary argon flow is via a third inlet passage comprising the passageway 27, the passageway 25, the chamber 14 and the passageway 13 to join the primary flow in the duct 8.

The pump 22 is then switched on, reducing the pressure in the chamber 16, opening the valve 17 and so reducing the pressure in the duct 8 and the valve cavity 2 below atmospheric. The valve 5 therefore lifts and a sample of gas is drawn in through the probe 3 along the duct 8 and exhausted via the pump 22. The sample passes over the filament 9 on which any organic volatile substances present are absorbed.

The primary argon flow continues and mixes with the sample, but owing to the relatively low rate of argon flow the sample is not significantly diluted. The secondary argon flow through the passageway 13 is effective to prevent any of the sample, and in particular any volatile substance not adsorbed on the filament 9 entering the chamber 14 and reaching the electron capture detector 23.

When a sufficient sample has been drawn through the apparatus, the pump 22 is switched off. The ball 17 is urged on to its seat by the spring 18 so that the first outlet valve is closed, and the pressure in the duct 8 and valve cavity 2 commences to rise in consequence of the continuing argon flows. The first inlet valve 5 is therefore closed, again sealing the first inlet passage 4. The argon escapes as before via the first outlet passage comprising the tube 20 and pump 22.

After a time sufficient for the argon flow to sweep any remaining traces of sample air from the duct 8, the solenoid 31 is energised, thus opening the second outlet valve 29. Since there is now a direct passage to atmosphere via second outlet passage comprising the passageway 13, the cavity 14, the passageway 25 and the tube 28, the pressure in the duct 3 drops to atmospheric and the ball valve 17 is closed by the action of the spring 18.

The filament 9 is now heated and any volatile organic substance contained in the gas sample which had been adsorbed thereon are driven off and are carried by the primary argon flow through the passageway 13 into the chamber 14, thus reaching the electron capture detector 23.

After a first sample has been examined in the manner described, the filament is allowed to cool and the valve 29 is closed. The apparatus is then in readiness for taking a second sample.

What is claimed is:

1. An apparatus for detecting a volatile organic substance contained in a gaseous mixture, comprising: (a) a chamber and an electron capture device disposed in said chamber of said apparatus, (b) a heatable filament which adsorbs, when cold, said volatile organic substance and when heated, releases said substance to said electron capture device, said apparatus further comprising a duct containing said filament, said duct communicating with said chamber, (c) a first inlet passage with a first inlet valve to admit a quantity of said mixture into the apparatus, said first inlet valve communicating with said duct and comprising means for opening said first inlet valve when the pressure in the apparatus is less than the ambient pressure and to close when the pressure in the apparatus exceeds the ambient pressure, (d) a second inlet passage that communicates with said duct and comprises means for admitting a primary flow of an inert gas over said filament, (e) a third inlet passage communicating with said chamber and comprising means for admitting a secondary flow of the inert gas which passes over the electron capture device when said filament is cold, (f) a first outlet passage with a first outlet valve to exhaust the gas under analysis and the inert gas to the atmosphere, said first outlet passage communicating with said duct. (g) a second outlet passage with a second outlet valve, said second outlet passage communicating with said chamber and comprising means for the primary flow of inert gas to take volatile components released from the filament when heated to the electron capture device, (h) means to open said first outlet valve of said first outlet passage when the pressure in the apparatus exceeds the ambient pressure, and (i) means to open said second outlet valve of said second outlet passage, the presence of one or more of the volatile organic substances being detected by a change in an output signal from the electron capture device.

2. An apparatus according to claim 1, further comprising a pump situated in said first outlet passage, said first inlet passage communicating with said first outlet passage via said duct wherein said first inlet valve of said first inlet passage is opened by lowering the pressure in the apparatus below the ambient pressure by said dump.

3. An apparatus according to claim 1, wherein said first outlet valve of said first outlet passage is a spring-loaded ball valve.

4. An apparatus according to claim 1, wherein said means to open the second outlet valve of said second outlet passage is an electrically operated solenoid valve, said apparatus comprising means for energising said solenoid valve when said filament is heated and the valves of the first inlet passage and the first outlet passage are closed.

5. An apparatus according to claim 1, in which said duct is present between said first and seocnd inlet passages and said chamber containing said electron capture device, and said filament is an electric element which is removably mounted in said duct between the first and the second inlet passages and the electron capture device.

6. An apparatus for controlling the flow of a gas mixture in which a quantity of the gas is drawn into the apparatus, comprising: (a) a filament which, when cold, adsorbs volatile organic substances contained in the gas and when heated, releases the volatile organic substances, to an electron capture device, (b) a first inlet passage with a first inlet valve to admit the quantity of said gas mixture into said apparatus, the first inlet valve of said first inlet passage being adapted to open when the pressure in the apparatus is less than the ambient pressure and to close when the pressure in the apparatus exceeds the ambient pressure, (c) a second inlet passage to admit a primary flow of an inert gas over said filament, (d) a third inlet passage to admit a secondary flow of said inert gas to pass over said electron capture device when said filament is cold, (e) a first outlet passage with a first outlet valve which exhausts the gas and the inert gas to the atmosphere, (f) a second outlet passage with a second outlet valve which permits the primary flow of inert gas to take the volatile components released from the filament when heated to the electron capture device, (g) means to open the first outlet valve when the pressure in the apparatus exceeds the pressure of the gas mixture drawn into the apparatus and (h) means to open the second outlet valve, wherein the presence of one or more of the volatile organic substances being detected by a change in an output signal from the electron capture device, whereafter a further quantity of gas is drawn into the apparatus via the first inlet passage.

7. An apparatus according to claim 6, further comprising a pump that is situated in the first outlet passage, said apparatus comprising means for opening said inlet valve by lowering the pressure in the apparatus below the pressure of the gas to be drawn into the apparatus by said pump.

8. An apparatus according to claim 6, in which said first outlet valve is a spring-loaded ball valve.

9. An apparatus according to claim 6, in which the means to open the second outlet valve is an electrically operated solenoid valve which is energised when said filament is heated and the valves of the first inlet passage and the first outlet passage are closed.

10. An apparatus according to claim 6, in which a duct is present between said first and second inlet passages and said chamber that contains said electron capture devices, wherein the filament is an electric element which is removably mounted in said duct between the first and the second inlet passages and the electron capture device.

* * * * *